(12) United States Patent
Tran (10) Patent No.: US 11,893,745 B2
(45) Date of Patent: Feb. 6, 2024

(54) SYSTEM AND METHOD FOR GENERATING AND DISPLAYING CONTOURS

(71) Applicant: RAYTHEON COMPANY, Waltham, MA (US)

(72) Inventor: Tuan T. Tran, Plano, TX (US)

(73) Assignee: RAYTHEON COMPANY, Waltham, MA (US)

( * ) Notice: Subject to any disclaimer, the term of this patent is extended or adjusted under 35 U.S.C. 154(b) by 324 days.

(21) Appl. No.: 17/116,878

(22) Filed: Dec. 9, 2020

(65) Prior Publication Data

US 2022/0180522 A1 Jun. 9, 2022

(51) Int. Cl.
| | |
|---|---|
| *G06T 7/13* | (2017.01) |
| *G06T 7/136* | (2017.01) |
| *G06T 11/20* | (2006.01) |
| *A61B 6/00* | (2006.01) |
| *A61B 5/055* | (2006.01) |
| *A61B 6/03* | (2006.01) |

(52) U.S. Cl.
CPC ............... *G06T 7/13* (2017.01); *A61B 6/463* (2013.01); *A61B 6/469* (2013.01); *A61B 6/5217* (2013.01); *G06T 7/136* (2017.01); *G06T 11/203* (2013.01); *A61B 5/055* (2013.01); *A61B 6/03* (2013.01); *G06T 2207/10081* (2013.01); *G06T 2207/10088* (2013.01); *G06T 2207/20092* (2013.01); *G06T 2207/30096* (2013.01)

(58) Field of Classification Search
None
See application file for complete search history.

(56) References Cited

U.S. PATENT DOCUMENTS

| | | |
|---|---|---|
| 5,425,368 A | 6/1995 | Brandt |
| 6,111,975 A | 8/2000 | Sacks et al. |
| 6,366,797 B1 | 4/2002 | Fisher et al. |
| 6,760,611 B1 | 7/2004 | Watanabe |
| 7,046,831 B2 | 5/2006 | Ruchala et al. |
| 8,265,357 B2 | 9/2012 | Ramsing et al. |
| 10,102,682 B1 | 10/2018 | Samaniego et al. |
| 10,186,062 B2 * | 1/2019 | Kim ....................... A61B 6/469 |

(Continued)

FOREIGN PATENT DOCUMENTS

| | | |
|---|---|---|
| DE | 10 2010 041 619 A1 | 3/2012 |
| JP | 2004-312434 A | 11/2004 |
| TW | 201123076 A1 | 7/2011 |

OTHER PUBLICATIONS

Badakhshannoory, et al., "A Model-Based Validation Scheme for Organ Segmentation in CT Scan Volumes", IEEE Transactions on Biomedical Engineering, vol. 58, No. 9 Sep. 1, 2011 (pp. 2681-2693).

(Continued)

*Primary Examiner* — Jeffrey J Chow
(74) *Attorney, Agent, or Firm* — LEWIS ROCA ROTHGERBER CHRISTIE LLP (57) ABSTRACT

A system and method for generating and displaying contours. In some embodiments, the method includes: calculating a first threshold, based on a first target point in a first slice; and generating a first contour, the first contour being a boundary of a first region, the first region being a region within which: the elements of the first slice are greater than the first threshold, or the elements of the first slice are less than the first threshold.

17 Claims, 4 Drawing Sheets

(56) References Cited

U.S. PATENT DOCUMENTS

| | | | |
|---|---|---|---|
| 10,706,539 | B2 | 7/2020 | Samaniego et al. |
| 2002/0097320 | A1* | 7/2002 | Zalis ............... G06T 7/0012 |
| | | | 382/130 |
| 2002/0136439 | A1 | 9/2002 | Ruchala et al. |
| 2004/0101184 | A1* | 5/2004 | Sivaramakrishna ...... G06T 7/12 |
| | | | 382/131 |
| 2004/0102905 | A1 | 5/2004 | Adorjan et al. |
| 2005/0232474 | A1 | 10/2005 | Wei et al. |
| 2005/0276455 | A1 | 12/2005 | Fidrich et al. |
| 2006/0082677 | A1* | 4/2006 | Donomae ............... G06T 5/008 |
| | | | 348/362 |
| 2006/0232608 | A1 | 10/2006 | Riaz |
| 2007/0127796 | A1* | 6/2007 | Nay ..................... G06V 10/46 |
| | | | 382/128 |
| 2007/0253617 | A1* | 11/2007 | Arata ..................... G06T 17/20 |
| | | | 382/154 |
| 2008/0026385 | A1 | 1/2008 | Sharma et al. |
| 2009/0080754 | A1* | 3/2009 | Tsuji ..................... H04N 25/62 |
| | | | 382/132 |
| 2009/0129653 | A1 | 5/2009 | DeHority et al. |
| 2009/0324078 | A1* | 12/2009 | Wu ......................... G06T 7/149 |
| | | | 382/173 |
| 2010/0246922 | A1 | 9/2010 | Uchihara et al. |
| 2010/0274119 | A1* | 10/2010 | Kabasawa ............. G06T 7/0012 |
| | | | 600/420 |
| 2011/0026798 | A1* | 2/2011 | Madabhushi .......... G01R 33/56 |
| | | | 382/131 |
| 2011/0135173 | A1 | 6/2011 | Elbaroudi et al. |
| 2011/0150309 | A1 | 6/2011 | Barfett et al. |
| 2011/0188722 | A1* | 8/2011 | Huang ................... G01R 33/56 |
| | | | 382/131 |
| 2012/0008860 | A1* | 1/2012 | Hirota ..................... G06T 7/11 |
| | | | 382/165 |
| 2012/0038644 | A1 | 2/2012 | Jones et al. |
| 2012/0207270 | A1 | 8/2012 | Flohr et al. |
| 2012/0212598 | A1 | 8/2012 | Mowrey et al. |
| 2013/0051676 | A1 | 2/2013 | Wehnes et al. |
| 2013/0202173 | A1* | 8/2013 | Buckler .................. G06T 7/143 |
| | | | 382/131 |
| 2013/0342668 | A1* | 12/2013 | Kasumi ............... A61B 1/0002 |
| | | | 348/74 |
| 2014/0099011 | A1* | 4/2014 | Begin ..................... G06T 5/002 |
| | | | 382/131 |
| 2014/0315732 | A1 | 10/2014 | Lobe |
| 2015/0004717 | A1 | 1/2015 | McDevitt et al. |
| 2015/0262359 | A1 | 9/2015 | Fujiwara et al. |
| 2015/0339809 | A1 | 11/2015 | Ohishi |
| 2016/0055632 | A1 | 2/2016 | Fu et al. |
| 2016/0080548 | A1 | 3/2016 | Erickson et al. |
| 2016/0135683 | A1* | 5/2016 | Yasuno ................ A61B 3/1233 |
| | | | 351/246 |
| 2017/0039725 | A1* | 2/2017 | Dror ......................... G06T 7/12 |
| 2017/0046848 | A1* | 2/2017 | Jo ............................ G06T 7/149 |
| 2017/0071562 | A1 | 3/2017 | Suzuki |
| 2017/0262600 | A1* | 9/2017 | Park ....................... G06T 7/0012 |
| 2018/0122067 | A1* | 5/2018 | Reicher .................. A61B 6/463 |
| 2018/0278868 | A1 | 9/2018 | Dawson et al. |
| 2018/0365808 | A1* | 12/2018 | Jiang ..................... G06T 7/0012 |
| 2019/0139223 | A1* | 5/2019 | Nie .......................... G06T 19/20 |
| 2019/0172205 | A1 | 6/2019 | Mao et al. |
| 2019/0370956 | A1* | 12/2019 | Jackson ................. A61B 6/503 |
| 2021/0042998 | A1 | 2/2021 | Samaniego |
| 2021/0150778 | A1* | 5/2021 | Elss ........................ A61B 6/032 |
| 2021/0169306 | A1* | 6/2021 | Oosake .............. A61B 1/00042 |
| 2021/0343008 | A1* | 11/2021 | Okuda ................... A61B 5/4836 |
| 2022/0037019 | A1* | 2/2022 | Covington ............ G16H 50/70 |

OTHER PUBLICATIONS

Cai, Jinzheng et al., "Pancreas Segmentation in CT and MRI Images via Domain Specific Network Designing and Recurrent Neural Contextual Learning", Mar. 30, 2018, pp. 1-11, arXiv:1803.11303v1.

Cai, Jinzheng et al., "Pancreas Segmentation in MRI Using Graph-Based Decision Fusion on Convolutional Neural Networks", 2016, pp. 442-450, Springer International Publishing AG.

European Patent Office Communication pursuant to Rules 161(1) and 162 EPC, dated Nov. 26, 2019, for Patent Application No. EP18706015.7, 3 pages.

Fishman, Elliot K. et al., "Volume Rendering versus Maximum Intensity Projection in CT Angiography: What Works Best, When, and Why", RadioGraphics, May-Jun. 2006, pp. 905-922, vol. 26, No. 3, RSNA.

International Search Report and Written Opinion of the International Searching Authority, dated Apr. 24, 2018, corresponding to PCT/US2018/015693, 12 pages.

International Search Report for corresponding International Application No. PCT/US2018/046564, filed Aug. 13, 2018, International Search Report dated Oct. 18, 2018 and dated Oct. 25, 2018 (5 pgs.).

International Search Report for corresponding International Application No. PCT/US2020/040319, filed Jun. 30, 2020, International Search Report dated Aug. 12, 2020 and dated Aug. 28, 2020 (5 pgs.).

Kauanova, Sholpan et al., "Automated image segmentation for detecting cell spreading for metastasizing assessments of cancer development", Jan. 1, 2018.

Kitano, S. et al., "Quantitative CT color mapping of the arterial enhancement fraction of the liver: A useful tool for the diagnosis of local hepatocellular carcinoma recurrences after TACE?", ECR, 2010, pp. 1-17, Poster No. C-0043, European Society of Radiology.

Mindek, Peter, "Maximum Intensity Projection Weighted by Statistical Cues", Proceedings of CESCG 2011, http://old.cescg.org/CESCG-2011/papers/TUBratislava-Mindek-Peter.pdf, retrieved Apr. 17, 2018, 7 pages.

Partial English translation of the Taiwanese Notice of Allowance, for Patent Application No. 107103473, dated Jul. 23, 2019, 1 page.

Persson, A. et al., "Standardized Volume Rendering for Magnetic Resonance Angiography Measurements in the Abdominal Aorta", Acta Radiologica, 2006, pp. 172-178, Taylor & Francis.

Simon, Inpakala et al., "Automated Image Analysis System for Detecting Boundaries of Live Prostate Cancer Cells", Cytometry, 1998, pp. 287-294, Wiley-Liss, Inc.

Taiwanese Notice of Allowance, for Patent Application No. 107103473, dated Jul. 23, 2019, 3 pages.

Unpublished U.S. Appl. No. 16/683,159, filed Nov. 13, 2019.
Unpublished U.S. Appl. No. 16/740,186, filed Jan. 10, 2020.
Unpublished U.S. Appl. No. 17/116,964, filed Dec. 9, 2020.

Written Opinion of the International Searching Authority for corresponding International Application No. PCT/US2018/046564, filed Aug. 13, 2018, Written Opinion of the International Searching Authority dated Oct. 25, 2018 (9 pgs.).

Written Opinion of the International Searching Authority for corresponding International Application No. PCT/US2020/040319, filed Jun. 30, 2020, Written Opinion of the International Searching Authority dated Aug. 28, 2020 (10 pgs.).

Younes, R. Ben et al., "A fully automated contour detection algorithm the preliminary step for scatter and attenuation compensation in SPECT", European Journal of Nuclear Medicine, 1988, pp. 586-589, Springer-Verlag.

Zhu, Zhuotun et al., "Multi-Scale Coarse-to-Fine Segmentation for Screening Pancreatic Ductal Adenocarcinoma", Jul. 9, 2018, pp. 1-9, arXiv:1807.02941v1.

Anonymous: "matlab—Extracting image region within boundary—Stack Overflow" retrieved from the Internet: URL:https://stackoverflow.com/questions/9442932/extracting-image-region-within-boundary, Mar. 2, 2012 (7 pgs.).

Anonymous: "Segmenting a cube in image by following the Coin segmentation tutorial. How to sort the blobs in a fixed order?—MATLAB Answers—MATLAB Central", retrieved from the Internet: URL:https://de.matworks.com/matlabcentral/answers/251547-segmenting-a-cube-in-image-by-following-the-coin-segmentation-tutorial-how-to-sort-the-blobs-in-a-f, Nov. 1, 2015 (8 pgs.).

(56) References Cited

OTHER PUBLICATIONS

Otsu N, "A Threshold Selection Method from Gray-Level Histograms", IEEE Transactions on Systems, Man and Cybernetics, IEEE Inc., vol. 9, No. 1, Jan. 1, 1979 (pp. 62-66).

Anonymous: "Region Growing problem with ginput—MATLAB Answers—MATLAB Central", retrieved from the Internet: URL:https://de.mathworks.com/matlabcentral/answers/82743-region-growing-problem-with-ginput, Nov. 6, 2017 (7 pgs.).

Anonymous: "How can i segment a color image with region growing?—MATLAB Answers—MATLAB Central", retrieved from the Internet: URL:https://de.mathworks.com/matlabcentral/answers/53351-how-can-i-segment-a-color-image-with-region-growing, Nov. 2, 2017 (5 pgs.).

Storyblocks: "Photoshop Basics: How to Use the Magic Wand Tool", retrieved from the Internet: URL:https://www.youtube.com/watch?v=cwh4CbsFxIA [retrieved on Mar. 5, 2021] frames at instant 0:34, 0:40 and 0:42, Nov. 24, 2015 (2 pgs.).

International Search Report for related International Application No. PCT/US2020/052566, filed Sep. 24, 2020, International Search Report dated Mar. 5, 2021 and dated Mar. 16, 2021 (4 pgs.).

Written Opinion of the International Searching Authority for related International Application No. PCT/US2020/052566, filed Sep. 24, 2020, Written Opinion of the International Searching Authority dated Mar. 16, 2021 (6 pgs.).

Avazpour, et al., "Segmentation of Extrapulmonary Tuberculosis Infection Using Modified Automatic Seeded Region Growing", Biological Procedures Online, Waterloo, CA, vol. 11, No. 1, Jul. 14, 2009 (pp. 241-252).

Nguyen, et al., "Plexiform Neurofibromas in Children with Neurofibromatosis Type 1: Frequency and Associated Clinical Deficits", Journal of Pediatrics, Mosby-Year Book, St. Louis, MO, US, vol. 159, No. 7, Apr. 7, 2011 (pp. 652-655).

International Search Report for corresponding International Application No. PCT/US2021/061218, filed Nov. 30, 2021, International Search Report dated Mar. 24, 2022 and dated Apr. 7, 2022 (5 pgs.).

Written Opinion of the International Searching Authority for corresponding International Application No. PCT/US2021/061218, filed Nov. 30, 2021, Written Opinion of the International Searching Authority dated Apr. 7, 2022 (6 pgs.).

* cited by examiner

SYSTEM AND METHOD FOR GENERATING AND DISPLAYING CONTOURS

FIELD

One or more aspects of embodiments according to the present disclosure relate to medical imaging, and more particularly to a system and method for drawing and displaying contours around one or more lesions in a medical imaging scan.

BACKGROUND

Medical imaging scans, such as magnetic resonance imaging (MRI) scans and computerized axial tomography (CT or CAT) scans are procedures that may be used to obtain information about the internal structure of an object, such as a patient.

In a medical imaging scan, a lesion, such as a cancerous portion of an organ, may have a different density than surrounding healthy tissue. It may be useful to determine a contour corresponding to the boundary between cancerous tissue and healthy tissue, so that, for example, the volume of a cancerous region may be estimated.

Drawing such a contour manually, e.g., by a radiologist operating a computer, may be time-consuming and imprecise, and the repeatability of such a method may be poor. Thus, there is a need for an improved system and method for generating contours in medical imaging scans.

SUMMARY

According to an embodiment of the present disclosure, there is provided a method for analyzing scan data, the method including: calculating a first threshold, based on a first target point in a first slice; and generating a first contour, the first contour being a boundary of a first region, the first region being a region within which: the elements of the first slice are greater than the first threshold, or the elements of the first slice are less than the first threshold.

In some embodiments, the method further includes calculating an outward slope at the first target point.

In some embodiments, the method further includes determining that the outward slope is less than zero, wherein the first region is a region within which the elements of the first slice are greater than the first threshold.

In some embodiments, the method further includes determining that the outward slope is greater than zero, wherein the first region is a region within which the elements of the first slice are less than the first threshold.

In some embodiments, the calculating of the outward slope includes; calculating a first statistic, of a first portion of the first slice, calculating a second statistic, of a second portion of the first slice, and calculating the outward slope based on the first statistic and the second statistic, wherein: the second portion of the first slice has more elements than the first portion of the first slice, and the second portion of the first slice includes the first portion of the first slice.

In some embodiments: the first statistic is an average, and the second statistic is an average.

In some embodiments, the method further includes: generating a second contour; displaying the first contour and the second contour to a user; and receiving an input from the user, selecting one of: the first contour, and the second contour.

In some embodiments, the method further includes generating a second contour in a second slice, based on a second target point in the second slice, wherein: the first slice is a first slice of a scan volume; and the second slice is a second slice of the scan volume, the second slice being adjacent to the first slice.

In some embodiments, the method further includes calculating the second target point based on the first contour.

In some embodiments: the calculating includes calculating the second target point as the centroid of the first contour, and the generating of the second contour includes generating the second contour in a search area centered on the second target point.

In some embodiments, the method further includes calculating the first threshold as an average over a first threshold-finding area of the first slice, the first threshold-finding area including the first target point.

In some embodiments, the method further includes: calculating a second threshold as an average over a second threshold-finding area, the second threshold-finding area being larger than, and containing, the first threshold-finding area; and generating a second contour, based on the second threshold.

According to an embodiment of the present disclosure, there is provided a non-transitory computer readable medium, the non-transitory computer readable medium storing instructions that, when executed by a processing circuit, cause the processing circuit to: calculate a first threshold, based on a first target point in a first slice; and generate a first contour, the first contour being a boundary of a first region, the first region being a region within which: the elements of the first slice are greater than the first threshold, or the elements of the first slice are less than the first threshold.

In some embodiments, the instructions further cause the processing circuit to calculate an outward slope at the first target point.

In some embodiments, the instructions further cause the processing circuit to determine that the outward slope is less than zero, wherein the first region is a region within which the elements of the first slice are greater than the first threshold.

In some embodiments, the instructions further cause the processing circuit to determine that the outward slope is greater than zero, wherein the first region is a region within which the elements of the first slice are less than the first threshold.

In some embodiments, the calculating of the outward slope includes; calculating a first statistic, of a first portion of the first slice, calculating a second statistic, of a second portion of the first slice, and calculating the outward slope based on the first statistic and the second statistic, wherein: the second portion of the first slice has more elements than the first portion of the first slice, and the second portion of the first slice includes the first portion of the first slice.

In some embodiments: the first statistic is an average, and the second statistic is an average.

In some embodiments, the instructions further cause the processing circuit to: generate a second contour; display the first contour and the second contour to a user; and receive an input from the user, selecting one of: the first contour, and the second contour.

According to an embodiment of the present disclosure, there is provided a system for generating a view of an interior of an object, the system including: a scanner for scanning the object; a processing circuit; and a display, the processing circuit being configured to: calculate a first threshold, based on a first target point in a first slice; and generate a first contour, the first contour being a boundary of a first region, the first region being a region within which:

the elements of the first slice are greater than the first threshold, or the elements of the first slice are less than the first threshold.

BRIEF DESCRIPTION OF THE DRAWINGS

Features, aspects, and embodiments are described in conjunction with the attached drawings, in which.

DETAILED DESCRIPTION

The detailed description set forth below in connection with the appended drawings is intended as a description of exemplary embodiments of a system and method for generating and displaying contours provided in accordance with the present disclosure and is not intended to represent the only forms in which the present disclosure may be constructed or utilized. The description sets forth the features of the present disclosure in connection with the illustrated embodiments. It is to be understood, however, that the same or equivalent functions and structures may be accomplished by different embodiments that are also intended to be encompassed within the scope of the disclosure. As denoted elsewhere herein, like element numbers are intended to indicate like elements or features.

A computerized axial tomography (CAT) scan is a procedure in which an object (e.g., a patient) is illuminated from several directions with penetrating (e.g., X-ray) radiation from a radiation source, and a scan image of the transmitted radiation is formed, in each instance, by a detector, to form a plurality of scan images, each of which may be represented as a two-dimensional array. The radiation may be attenuated at different rates in different kinds of matter; accordingly, each point in each image may correspond to a transmitted radiant intensity depending on the attenuation rates of the compositions of matter on the path along which the radiation traveled from the radiation source to the detector. From the combination of scan images, raw scan data, e.g., a three-dimensional model of the "density" of the object (which may be referred to as a three-dimensional scan data array) may be formed.

As used herein, the "density" within an object is any characteristic that varies within the object and that is measured by the medical imaging scan. For example, with respect to CAT scans, the "density" may refer to the local rate of attenuation of the penetrating radiation, and with respect to MRI scans, the "density" may refer to the density of atoms having a nuclear resonance at the frequency of the probe radio frequency signal, in the presence of the magnetic field being applied.

Although some examples are discussed in the present disclosure in the context of CAT scans or MRI scans of a human patient, the disclosure is not limited thereto, and in some embodiments other kinds of scans providing three-dimensional density data such as positron emission tomography scans, or scans of objects other than human patients, may be processed in an analogous fashion. In the case of other kinds of scans, density may be defined accordingly; in the case of a positron emission tomography scan, for example, the density may be the density of nuclei that decay by beta plus emission. As used herein, the term "object" includes anything that may be scanned, and encompasses without limitation human patients, animals, plants, inanimate objects, and combinations thereof.

When the object being imaged is a human patient (or other living object), a contrast agent may be used (e.g., injected into or ingested by the patient) to selectively alter the density of some tissues. The contrast agent may for example include a relatively opaque substance (i.e., relatively opaque to the penetrating radiation). The density of tissue containing the contrast agent may be increased as a result, and it may be increased to an extent that depends on the concentration of contrast agent in the tissue. The concentration of the contrast agent may initially increase in the tissue, and then gradually decrease again, and the density of the tissue may similarly increase initially and, then decrease.

Figure 1:
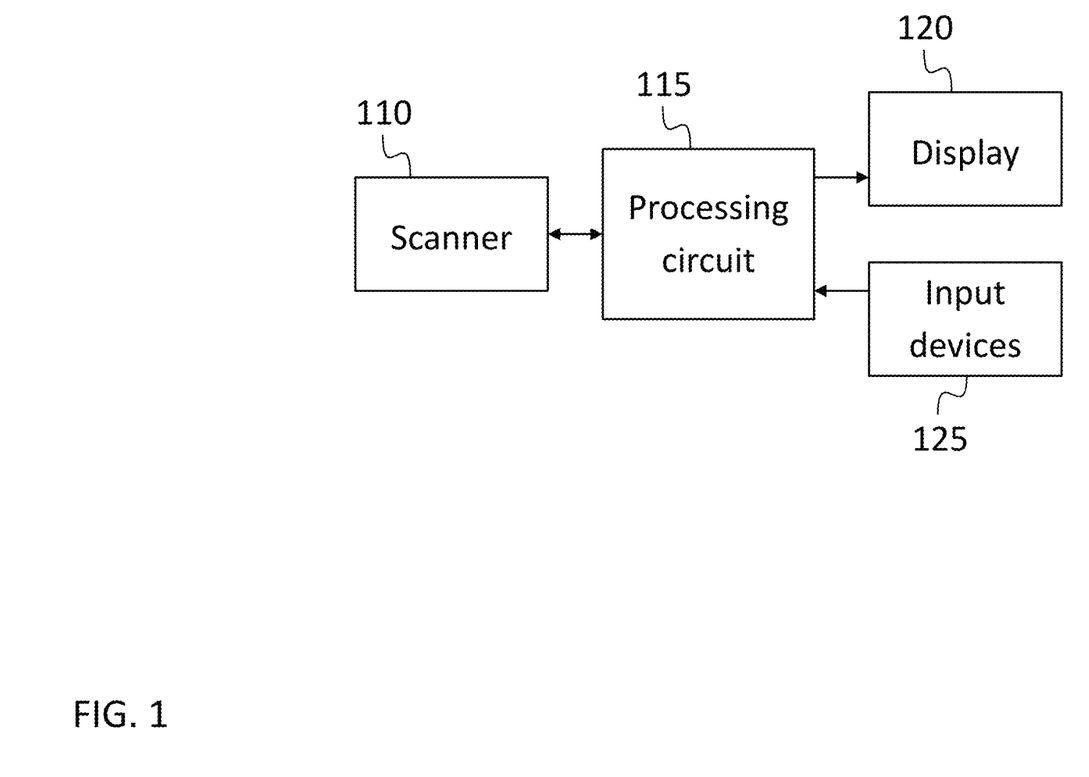
FIG. 1 is a block diagram of a system for performing and analyzing a medical imaging scan, according to an embodiment of the present disclosure.

FIG. 1 shows a block diagram of a system for performing a scan and processing and displaying the results, according to one embodiment. The system includes a scanner 110, a processing circuit 115 (described in further detail below), a display 120 for displaying images, or sequences of images in the form of a movie (or "video"), and one or more input devices 125 such as a keyboard or mouse, that an operator, or "user" (e.g., a radiologist) may use to operate the system, and to set parameters affecting the processing of the images to be displayed. It should be noted that the processing circuit 115, the display 120, and the input devices 125 may be part of a unitary system or may be a distributed system with the processing circuit 115, for example, being separate and communicatively coupled to the display 120 and input devices 125. In some embodiments, servers store the images and clients request and receive the images from the servers, with image processing performed on the server or on the client, or both.

A plurality of scans may be performed, and analyzed together. For example, a first scan of an object (e.g., a patient) may be performed before the contrast agent is injected, and several subsequent scans of the object may be performed at various times (e.g., at regular intervals) after injection of the contrast agent, as the concentration of contrast agent changes. The rate at which the concentration of contrast agent increases initially, the peak concentration reached, and the rate at which the concentration of contrast agent subsequently decreases all may depend on the type of tissue into which the contrast agent is injected or which is of interest. In some embodiments, the three-dimensional scan data arrays that result from several scans, performed at different intervals after the injection of the contrast agent, may be processed together e.g., subtracted from each other pairwise, to form further three-dimensional scan data arrays. These arrays may then be analyzed, as described herein, e.g., contours and surfaces may be generated based on the three-dimensional scan data arrays, and the contours may be displayed, overlaid on slices (e.g., on two-dimensional data arrays composed of elements selected from the three-dimensional scan data arrays).

As used herein, a "slice" is a two-dimensional scan data array formed along a surface within a three-dimensional scan data array. For example, for a three-dimensional scan data array for a patient, three axes may be defined, an "axial" axis (e.g., parallel to a longitudinal direction of the patient), a "coronal" axis (e.g., an axis parallel to the front-rear direction in the patient) and a "sagittal" axis (e.g., an axis parallel to a left-right direction in the patient). Planes, and slices, may then be defined, with corresponding names, perpendicular to the respective axes. For example, an axial slice may be a two-dimensional subarray perpendicular to the axial axis, e.g., consisting of all of the elements of the three-dimensional scan data array at a certain position along the axial axis. The elements of a slice may also be referred to as "pixels". The terms "axial", "sagittal" and "coronal" are not limited, as used herein, to being parallel to the longitudinal direction of the patient, the left-right direction in the patient, and the front-rear direction in the patient respectively; instead these terms may refer to any substantially orthogonal directions (e.g., three directions, any pair of which is within 15 degrees of being perpendicular).

The three-dimensional scan data array generated by a medical imaging scan may include portions or features not relevant for the subsequent analysis to be performed. For example, if a medical imaging scan is being performed to check for, or characterize, a lesion (e.g., a cancerous lesion) within the torso of a patient, then the arms of the patient, or the buckle of a belt worn by the patient, may be present in the three-dimensional scan data array. Such features may interfere with subsequent analysis, and as such, it may be advantageous to exclude them. As such, in some embodiments, a torso contour (a contour that approximates the boundary of a patient's torso) may be generated in one or more slices, and elements of the three-dimensional scan data array that fall outside of the torso contour (or outside a rectangle containing the torso contour) may be disregarded.

In some embodiments, the generating of the torso contour may proceed as follows. Within a scan volume consisting of a set of consecutive axial slices (e.g., a set of slices corresponding approximately to a certain portion of the patient, e.g., the portion of the torso below the diaphragm), a central slice may be selected, and within the central slice, a central row and a central column may be selected. As used herein, "central" means within the middle one-third, e.g., for a set of 30 slices, a central slice is one selected from the range extending from the $10^{th}$ slice to the $20^{th}$ slice. A plurality of maximum values may then be calculated, each of the maximum values being the maximum value within a respective slice of the set of consecutive axial slices. The median of these maximum values may then be used to set a threshold (e.g., the threshold may be set to be equal to a constant factor times the median).

Within the central slice, a first rectangle may then be defined, based on the threshold. The first rectangle may have a left edge at the first peak, in order, of two or more horizontal peaks exceeding the threshold in the central row. As used herein, "first . . . in order" refers to the first element in an ordered set of elements, and "last . . . in order" refers to the last element in an ordered set of elements. For example, the first element of an array of N elements may be referred to as the first element, in order, of the array, and the $N^{th}$ element may be referred to as the last element, in order, of the array. When used without the qualifying phrase "in order", the modifier "first" is used herein only to distinguish an element from other similar elements, which may be referred to as "second", "third", and the like, and which may follow or precede the first element, if the elements are ordered. As used herein, a "peak" is a local maximum, i.e., an element having a smaller neighbor on each side. A "horizontal peak" is a local maximum in a row, and a "vertical peak" is a local maximum in a column.

Figure 2:
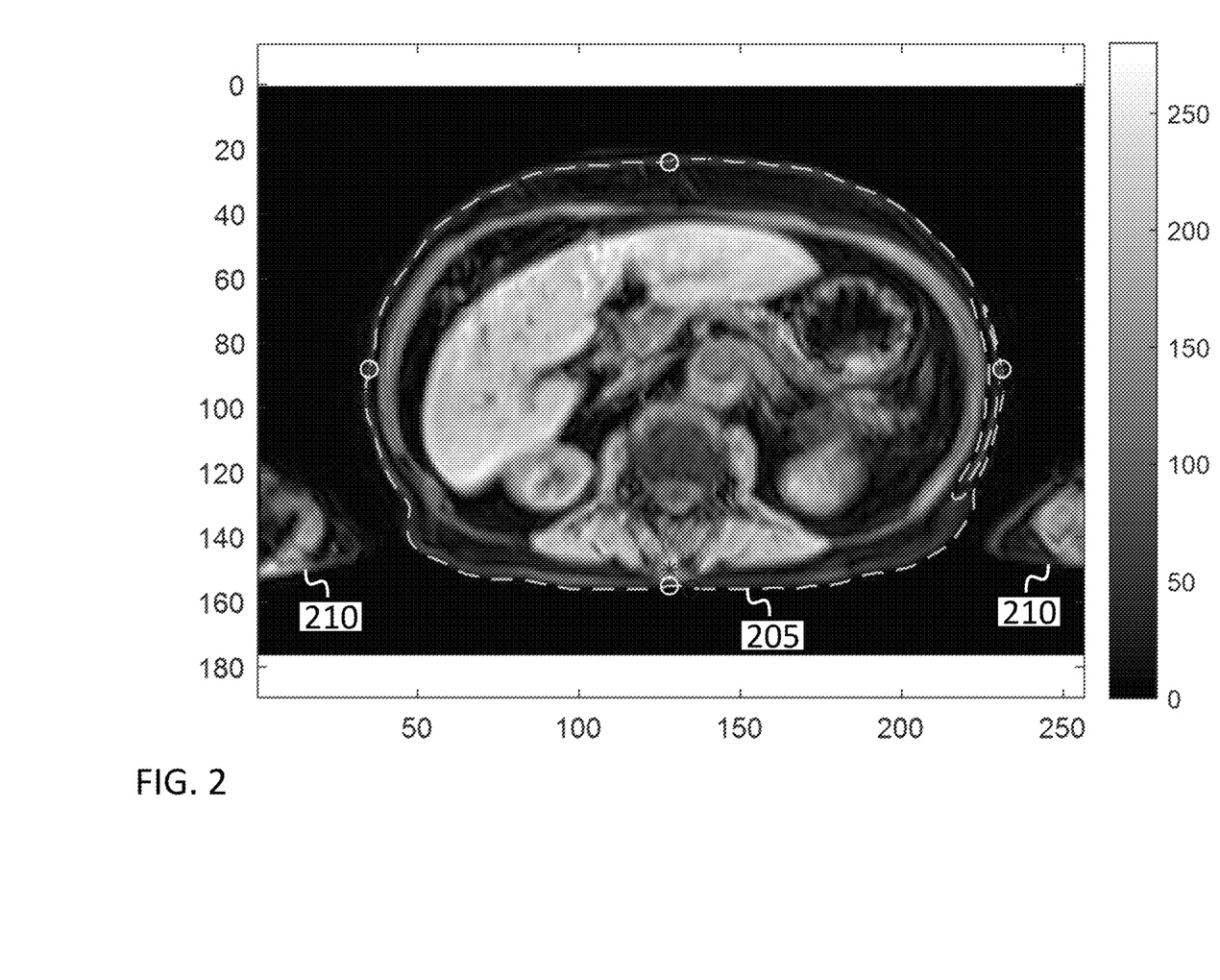
FIG. 2 is a view of an axial slice of an imaging scan, according to an embodiment of the present disclosure.

The first rectangle may further have a right edge at the last peak, in order, of the two or more horizontal peaks exceeding the threshold in the central role. It may also have a top edge at a first peak, in order, of two or more vertical peaks exceeding the threshold in the central column, and a bottom edge at the last peak, in order, of the two or more vertical peaks. The first rectangle may then be used to adjust the threshold, as follows. First, a second plurality of maximum values may be calculated over the set of slices, each maximum value being the maximum value within the first rectangle in the respective slice, of the set of slices. The adjusted threshold may then be used to generate the torso contour, by finding a region of the central slice within which the values exceed the second threshold, and defining the torso contour to be the boundary of this region (or the boundary of the largest such region, if there are several). FIG. 2 shows an example of a torso contour 205, in a slice that also contains the patients arms 210. In the example of FIG. 2, the arms are smaller than the torso and therefore neither arm is identified as the torso.

Some scan data, such as computerized tomography scan data, may include other artifacts that may be removed, as follows, before generating the torso contour. Such artifacts, may be caused, for example, by the presence of a table supporting the patient during the scan; such a table may have a sheet metal upper surface, for example, that may appear as a white (high density) line in an image of a slice from the scan. In some embodiments, the removal of such artifacts proceeds as follows. First a horizontal moving sum is calculated along the central row, and an analogous, vertical, moving sum is calculated along the central column. The width of the filter used for the moving sums may be selected to be comparable to or wider than a characteristic thickness of the artifacts to be removed, e.g., the thickness of the sheet metal upper surface of the table.

A rectangle, to be used as a mask, may then be defined, based on a preset threshold. The rectangle may have a left edge, at a first value, in order, within the horizontal moving sum, exceeding the threshold; a right edge, at the last value, in order, within the horizontal moving sum, exceeding the threshold; a top edge, at a first value, in order, within the vertical moving sum, exceeding the threshold; and a bottom edge, at the last value, in order, within the vertical moving sum, exceeding the third threshold. The rectangle may then (as mentioned above) be used as a mask, and the torso contour may be drawn entirely within the second rectangle, thereby avoiding inclusion of artifacts. In addition to making possible the exclusion of features (e.g., arms or a table) outside of the patient's torso, the finding of a torso contour may be helpful for determining the size of the patient. This size may be used to apply suitable scaling, in methods, discussed below, for determining the contour of a lesion. As used herein, unless otherwise specified (as in the phrase "torso contour"), a "contour" refers to a candidate contour corresponding to the boundary, in a slice, of a lesion or suspected lesion.

Contours may be generated around areas suspected of containing lesions around a target point, as follows. The target point may be a pixel (selected by the user, as a point within a suspected lesion) in a reference slice (which may also be selected by the user, e.g., by stepping through the slices as they are each displayed in sequence).

A suspected lesion may include tissue that is of higher density than the surrounding tissue, or it may include tissue that is of lower density than surrounding tissue. Contours around both types of lesion may be drawn, by first calculating an outward slope. As used herein, an outward slope is a measure that returns a positive value at a local minimum and a negative value at a local maximum. Such a slope may be calculated, at the target point, as follows. First, an average over a first area containing the target point may be calculated. Then, the average over a second area, larger than the first area, and including the first area (and including the target point), may be calculated. The difference between the two averages may then be used to calculate the outward slope (e.g., the outward slope may be the average over the second area minus the average over the first area). For example, if the average over the second area is greater than the average over the first area (as would be expected if the target point is a local minimum), the outward slope may be positive. As used herein, an "average" may be a weighted average, or a straight average (i.e., a weighted average in which the weights are all equal to one).

The contour of the lesion in the reference slice may be calculated as the boundary of a region, within the reference slice, consisting of pixels that either exceed a first threshold, or are less than the first threshold, depending on whether the previously calculated outward slope is positive or negative. For example, if the previously calculated outward slope is greater than zero, then a region of pixels less than the first threshold may be used; if the previously calculated outward slope is less than zero, then a region of pixels greater than the first threshold may be used. In this manner, the contour-generating method is capable of producing a meaningful contour regardless of whether the lesion consists of tissue having higher density, or lower density, than the surrounding tissue.

Contours (e.g., candidate lesion contours) may be generated using an iterative approach in which each of (i) the first threshold, (ii) a threshold-finding area and (iii) a search area is incrementally adjusted over a number of iterations, each iteration generating an additional candidate contour. A user may then view the candidate contours and select one that, in the user's opinion, is the best fit to the probable boundary of the lesion.

The threshold-finding area and the search area may each be initialized to a preset area around the target point (e.g., the threshold-finding area may be initialized to a rectangular area centered on the target point, and the search area may be initialized to an elliptical area centered on the target point). The size of the preset area may be scaled to the size of the patient, based on the finding of a torso contour, as mentioned above. The threshold may then be calculated as a statistic (e.g., an average) over the threshold-finding area, and used to generate one or more contours (each being a boundary of a region within which the scan data values exceed the threshold (for a high-density lesion) or fall below the threshold (for a low-density lesion)). The boundary including the target point (or the boundary enclosing the largest area, if no boundary includes the target point) may then be saved as a candidate contour, and one or both of the threshold-finding area and the search area may be increased (e.g., by an amount based on the size of the smallest rectangle including all of the contours found for the present threshold value), in preparation for generating the next contour. This process may be repeated multiple times, with, in each iteration, the updated threshold being based on the updated threshold-finding area. One or more masks may be used, in the process of finding the threshold or in the process of finding contours, to avoid capturing, within any contour or within the threshold-finding data, regions (e.g., regions outside the patient) that are not candidates for containing lesions.

In some embodiments, the changing of the threshold is stopped or limited after a fixed number of iterations (e.g., after two iterations) or after the threshold has been changed during a certain number of previous iterations. For example, when the threshold was adjusted both on the previous iteration, and on the iteration preceding the previous iteration, a flag (which may be referred to as a "freeze flag") may be set. When the freeze flag is set (e.g., on subsequent iterations), the threshold-finding area may be left unchanged, and the threshold may be changed by a fixed amount (e.g., by a fraction of (e.g., 20% of) the amount by which the threshold was changed on a previous iteration, when the freeze flag was not set). The use of a freeze flag may avoid a situation in which the contours grow to enclose large amounts of normal tissue outside of the lesion.

The contours may then be displayed (e.g., simultaneously, or one at a time) to a user, who, as mentioned above, may select a contour that, in the user's opinion, is the best fit to the probable boundary of the lesion. The threshold corresponding to this contour, the sign of the outward slope, and the centroid of the area enclosed by the centroid, may be saved for use in finding a contour in an adjacent slice, as discussed in further detail below.

A contour may then be found in an adjacent slice, by finding the boundary of a region, within a search area in the adjacent slice, consisting of pixels that either exceed the first threshold, or are less than the first threshold, depending on whether the previously calculated outward slope is negative or positive, respectively (i.e., whether the lesion is a high-density lesion or a low-density lesion, respectively). The search area may be an area (e.g., an elliptical area) containing (e.g., centered on) the centroid of the reference slice. This process may be repeated on further slices (e.g., on a slice adjacent to the slice adjacent to the reference slice), each time using the centroid of the area enclosed by the contour in one slice as the target point (for selecting the search area) in an adjacent slice. The process may be repeated for all of the slices of interest on one side of the reference slice (e.g., all of the slices of interest above (i.e., nearer to the head of the patient than) the reference slice), and the process may also be repeated for all of the slices of interest on the other side of the reference slice (e.g., nearer to the feet of the patient than the reference slice). A plurality of respective contours, in a contiguous set of slices, may then define a surface of the volume of the lesion (e.g., each of the plurality of contours may be in the surface of the volume of the lesion).

Figure 3A:
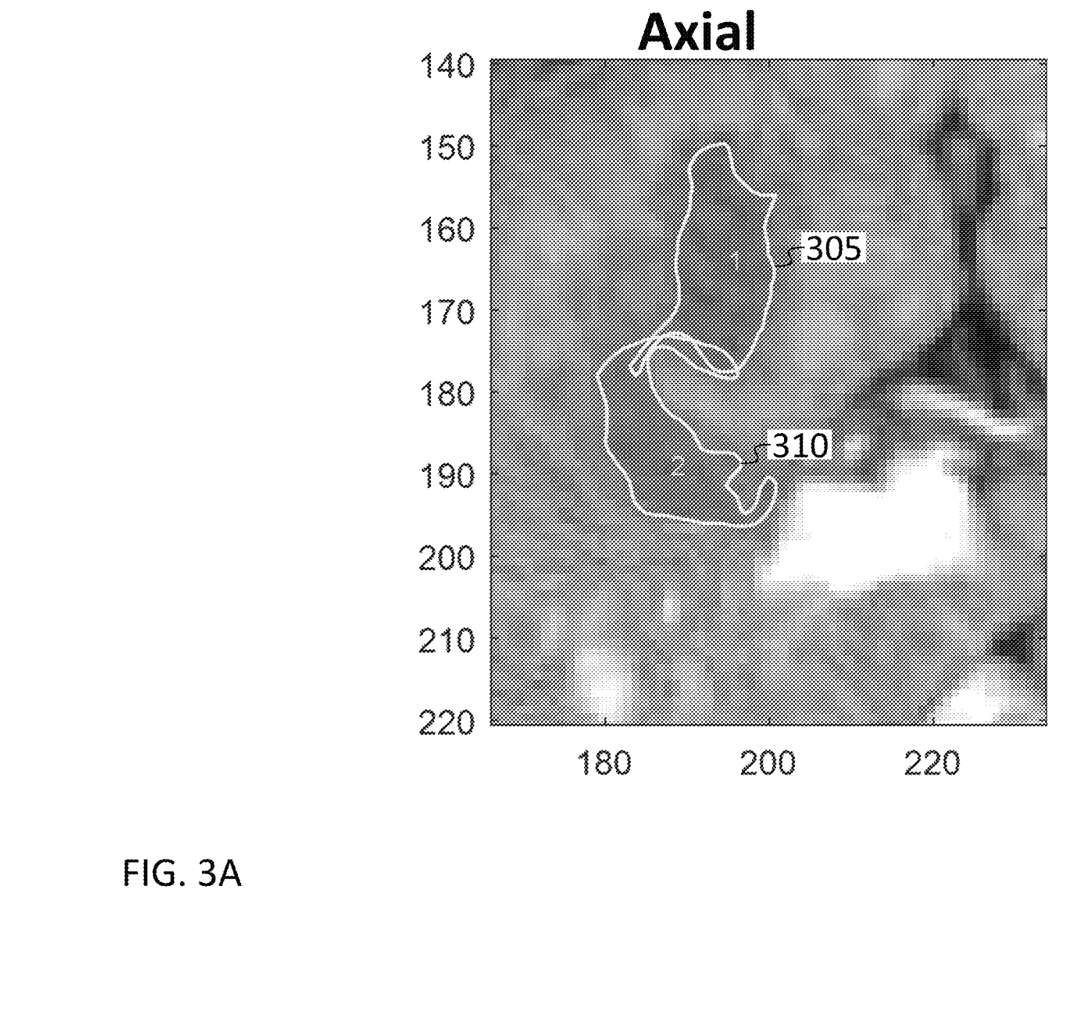
FIG. 3A is a view of an axial slice of an imaging scan, according to an embodiment of the present disclosure.
Figure 3B:
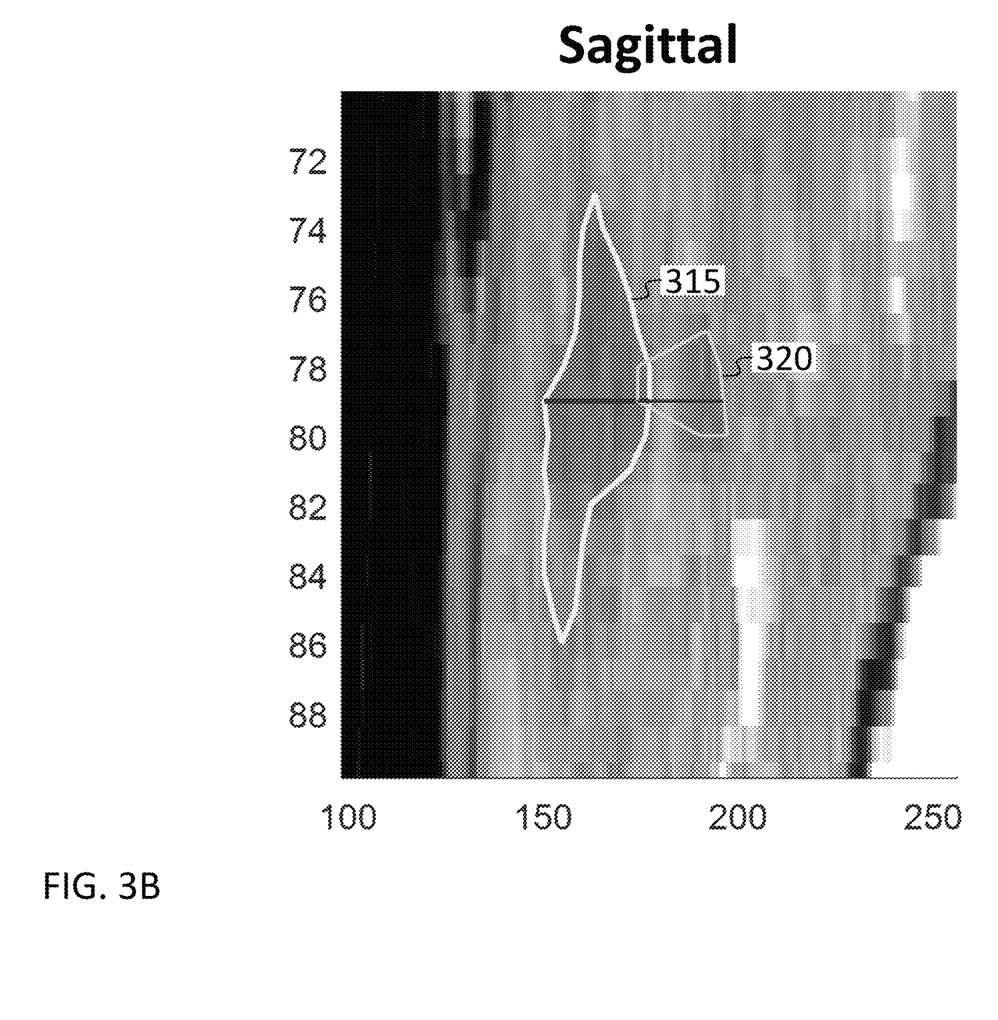
FIG. 3B is a view of a sagittal slice of an imaging scan, according to an embodiment of the present disclosure.

The methods described herein may be used for a plurality of lesions, e.g., each identified by the user by designating a respective target point in the reference slice. For example, a plurality of first axial contours may be generated, for each of a first plurality of axial slices, the plurality of first axial contours defining a first volume (the volume of a first lesion), and a plurality of second axial contours may be generated, for each of a second plurality of axial slices (which may be the same as the first plurality of axial slices), the plurality of second axial contours defining a second volume (the volume of a second lesion). The contour of the first volume and the contour of the second volume may then be calculated in another slice (e.g., a sagittal slice) and displayed, overlaid on the sagittal slice. FIG. 3A shows an axial slice in which a first contour 305, showing the boundary of a first lesion, and a second contour 310, showing the boundary of a second lesion, have been overlaid on an image of the slice. In some embodiments, contours around the same lesions may be shown in other (e.g., orthogonal) slices, annotated or color-coded to identify the correspondence between the contours in the axial slice and the contours in the perpendicular slice. For example, FIG. 3B shows a sagittal view, for a sagittal slice passing through the target point of the reference slice, showing the same two lesions as those of FIG. 3A, with a first sagittal contour 315 being on the surface of the volume of the first lesion, and a second sagittal contour 320 being on the surface of the volume of the second lesion. The correspondence between the contours in FIG. 3B and those in FIG. 3A may be indicated by the color of the contours in FIG. 3B; for example, the first contour 315 in FIG. 3B may be displayed in yellow, and the second contour 320 may be displayed in cyan. An analogous coronal view may be generated and displayed in a similar manner. Such a view may show a coronal slice passing through the target point of the reference slice, and, overlaid on the image of the coronal slice, contours of the same two lesions as those of FIG. 3A, with a first coronal contour being on the surface of the volume of the first lesion, and a second coronal contour being on the surface of the volume of the second lesion.

As used herein, "a portion of" something means "at least some of" the thing, and as such may mean less than all of, or all of, the thing. As such, "a portion of" a thing includes the entire thing as a special case, i.e., the entire thing is an example of a portion of the thing. As used herein, the term "rectangle" includes a square as a special case, i.e., a square is an example of a rectangle, and the term "rectangular" encompasses the adjective "square". As used herein, when a second number is "within Y%" of a first number, it means that the second number is at least (1−Y/100) times the first number and the second number is at most (1+Y/100) times the first number. As used herein, the word "or" is inclusive, so that, for example, "A or B" means any one of (i) A, (ii) B, and (iii) A and B. As used herein, the term "array" refers to an ordered set of numbers regardless of how stored (e.g., whether stored in consecutive memory locations, or in a linked list).

The term "processing circuit" is used herein to mean any combination of hardware, firmware, and software, employed to process data or digital signals. Processing circuit hardware may include, for example, application specific integrated circuits (ASICs), general purpose or special purpose central processing units (CPUs), digital signal processors (DSPs), graphics processing units (GPUs), and programmable logic devices such as field programmable gate arrays (FPGAs). In a processing circuit, as used herein, each function is performed either by hardware configured, i.e., hard-wired, to perform that function, or by more general-purpose hardware, such as a CPU, configured to execute instructions stored in a non-transitory storage medium. A processing circuit may be fabricated on a single printed circuit board (PCB) or distributed over several interconnected PCBs. A processing circuit may contain other processing circuits; for example, a processing circuit may include two processing circuits, an FPGA and a CPU, interconnected on a PCB.

As used herein, when a method (e.g., an adjustment) or a first quantity (e.g., a first variable) is referred to as being "based on" a second quantity (e.g., a second variable) it means that the second quantity is an input to the method or influences the first quantity, e.g., the second quantity may be an input (e.g., the only input, or one of several inputs) to a function that calculates the first quantity, or the first quantity may be equal to the second quantity, or the first quantity may be the same as (e.g., stored at the same location or locations in memory as) the second quantity.

Although limited embodiments of a system and method for generating and displaying contours have been specifically described and illustrated herein, many modifications and variations will be apparent to those skilled in the art. Accordingly, it is to be understood that a system and method for generating and displaying contours employed according to principles of this disclosure may be embodied other than as specifically described herein. The disclosure is also defined in the following claims, and equivalents thereof.

What is claimed is:

1. A method for analyzing scan data, the method comprising:
   calculating a first threshold, based on a median of a plurality of maximum values in a first target point in a first slice;
   generating a first contour for the first slice,
   the first contour being a boundary of a first region,
   the first region being a region within which:
      elements of the first slice are greater than the first threshold, or
      the elements of the first slice are less than the first threshold;
   generating a centroid for the first contour and saving the generated centroid in a memory;
   generating a second contour in a second slice, based on a second target point in the second slice, wherein:
      the first slice is a first slice of a scan volume, and
      the second slice is a second slice of the scan volume, the second slice being adjacent to the first slice, and wherein
      the second target point is calculated as the centroid of the first contour saved in the memory, and the generating of the second contour comprises generating the second contour in a search area centered on the second target point; and
   removing artifacts from the first slice by calculating a horizontal moving sum along a row of the first slice and a vertical moving sum along a column of the first slice, and selecting a moving filter for the moving sums to be comparable to or wider than a thickness of the artifacts to be removed to remove the artifacts.

2. The method of claim 1, further comprising calculating an outward slope at the first target point.

3. The method of claim 2, further comprising determining that the outward slope is less than zero,
   wherein the first region is a region within which the elements of the first slice are greater than the first threshold.

4. The method of claim 2, further comprising determining that the outward slope is greater than zero,
   wherein the first region is a region within which the elements of the first slice are less than the first threshold.

5. The method of claim 2, wherein the calculating of the outward slope comprises;
   calculating a first statistic, of a first portion of the first slice,
   calculating a second statistic, of a second portion of the first slice, and
   calculating the outward slope based on the first statistic and the second statistic,
   wherein:
      the second portion of the first slice has more elements than the first portion of the first slice, and
      the second portion of the first slice includes the first portion of the first slice.

6. The method of claim 5, wherein:
   the first statistic is an average, and
   the second statistic is an average.

7. The method of claim 6, further comprising:
   displaying the first contour and the second contour to a user; and
   receiving an input from the user, selecting one of:
      the first contour, and the second contour.

8. The method of claim 1, further comprising calculating the first threshold as an average over a first threshold-finding area of the first slice, the first threshold-finding area including the first target point.

9. The method of claim 8, further comprising:
calculating a second threshold as an average over a second threshold-finding area, the second threshold-finding area being larger than, and containing, the first threshold-finding area; and
generating the second contour, based on the second threshold.

10. A non-transitory computer readable medium, the non-transitory computer readable medium storing instructions that, when executed by a processing circuit, cause the processing circuit to:
calculate a first threshold, based on a median of a plurality of maximum values in a first target point in a first slice;
generate a first contour,
the first contour being a boundary of a first region,
the first region being a region within which:
elements of the first slice are greater than the first threshold, or
the elements of the first slice are less than the first threshold;
generating a centroid for the first contour and saving the generated centroid in a memory;
generating a second contour in a second slice, based on a second target point in the second slice, wherein:
the first slice is a first slice of a scan volume, and
the second slice is a second slice of the scan volume, the second slice being adjacent to the first slice, and wherein
the second target point is calculated as the centroid of the first contour, and the generating of the second contour comprises generating the second contour in a search area centered on the second target point; and
remove artifacts from the first slice by calculating a horizontal moving sum along a row of the first slice and a vertical moving sum along a column of the first slice, and selecting a moving filter for the moving sums to be comparable to or wider than a thickness of the artifacts to be removed to remove the artifacts.

11. The non-transitory computer readable medium of claim 10, wherein the instructions further cause the processing circuit to calculate an outward slope at the first target point.

12. The non-transitory computer readable medium of claim 11, wherein the instructions further cause the processing circuit to determine that the outward slope is less than zero,
wherein the first region is a region within which the elements of the first slice are greater than the first threshold.

13. The non-transitory computer readable medium of claim 11, wherein the instructions further cause the processing circuit to determine that the outward slope is greater than zero,
wherein the first region is a region within which the elements of the first slice are less than the first threshold.

14. The non-transitory computer readable medium of claim 11, wherein the calculating of the outward slope comprises;
calculating a first statistic, of a first portion of the first slice,
calculating a second statistic, of a second portion of the first slice, and
calculating the outward slope based on the first statistic and the second statistic,
wherein:
the second portion of the first slice has more elements than the first portion of the first slice, and
the second portion of the first slice includes the first portion of the first slice.

15. The non-transitory computer readable medium of claim 14, wherein:
the first statistic is an average, and
the second statistic is an average.

16. The non-transitory computer readable medium of claim 15, wherein the instructions further cause the processing circuit to:
display the first contour and the second contour to a user; and
receive an input from the user, selecting one of:
the first contour, and the second contour.

17. A system for generating a view of an interior of an object, the system comprising:
a scanner for scanning the object;
a processing circuit; and
a display,
the processing circuit being configured to:
calculate a first threshold, based on a median of a plurality of maximum values in a first target point in a first slice; and
generate a first contour,
the first contour being a boundary of a first region,
the first region being a region within which:
elements of the first slice are greater than the first threshold, or
the elements of the first slice are less than the first threshold;
generate a centroid for the first contour and save the generated centroid in a memory;
generate a second contour in a second slice, based on a second target point in the second slice, wherein:
the first slice is a first slice of a scan volume, and
the second slice is a second slice of the scan volume, the second slice being adjacent to the first slice, and wherein
the processing circuit calculates the second target point as the centroid of the first contour, and generates the second contour by generating the second contour in a search area centered on the second target point; and
remove artifacts from the first slice by calculating a horizontal moving sum along a row of the first slice and a vertical moving sum along a column of the first slice, and selecting a moving filter for the moving sums to be comparable to or wider than a thickness of the artifacts to be removed to remove the artifacts.

\* \* \* \* \*